United States Patent

Lietaer

Patent Number: 5,330,355
Date of Patent: Jul. 19, 1994

[54] ENDODONTIC ANGLE-PIECE

[75] Inventor: Eric Lietaer, Sallanches, France

[73] Assignee: Anthogyr, société anonyme, Sallanches, France

[21] Appl. No.: 952,821
[22] PCT Filed: May 28, 1990
[86] PCT No.: PCT/FR90/00750
    § 371 Date: Nov. 23, 1992
    § 102(e) Date: Nov. 23, 1992
[87] PCT Pub. No.: WO91/18555
    PCT Pub. Date: Dec. 12, 1991
[51] Int. Cl.$^5$ ............................................. A61C 1/18
[52] U.S. Cl. .................................... 433/112; 433/122
[58] Field of Search ............... 433/102, 112, 118, 122, 433/133

[56] References Cited

U.S. PATENT DOCUMENTS 2,135,933  11/1938  Blair ............................ 433/122 X
5,040,977  8/1991  Weissman ..................... 433/122
5,169,312  12/1992  Berlin ........................... 433/112 X

FOREIGN PATENT DOCUMENTS 69564  7/1941  Czechoslovakia ............ 433/122
873251  7/1942  France ......................... 433/112

Primary Examiner—Gene Mancene
Assistant Examiner—Nicholas D. Lucchesi
Attorney, Agent, or Firm—William H. Eilberg

[57] ABSTRACT

A dental apparatus provided with a drive unit for operative dentistry instruments, specifically a powered system for performing the various phases of operative dentistry operations. This advanced dental apparatus is essentially characterized in that the working tool housed in a tool-holder sleeve, exhibits dampable, disengageable, reciprocating helical motion using a flexible cam. The cam is mounted on the rotational axis and its end is received in a hole in the sleeve. This device allows completely safe operative dentistry operations to be performed, while preventing false canals and instrument breakage, through the use of the flexible movement control device.

11 Claims, 2 Drawing Sheets

ENDODONTIC ANGLE-PIECE

The present invention relates to dental equipment which has a drive unit for endodontic instruments or, more accurately, a mechanised system that can be used during the various phases of work relating to endodontic treatment.

It is well known that these various phases are very awkward because of the extremely wide variety of shapes of root canals depending on the teeth involved (canine, incisor, premolar and molar).

Many items of equipment, as described in the patent documents EP-A-230 846, EP-A-0 161 196, FR-A-2 178 349 are known for accomplishing various endodontic procedures; they provide alternating angular movements that may or may not be combined with longitudinal straight movements involving various alternatives in terms of the amplitude of movement or the degrees of freedom that the instrument has when working.

These types of equipment provide incomplete, non-progressive damping of the movements of the instrument either by permanent backlash deliberately created in the means of transmitting the movement or by a disengaging system that acts if the instrument is overloaded.

A large number of these types of equipment have the following problems:

significant modification of the apical third on curved root canals;

producing false root canals;

frequent breakage of instruments when they become jammed.

All the above items of equipment attempted to replace manual operation by mechanised systems but did not afford the practitioner the necessary adequate safety when carrying out endodontic treatment.

The present invention adds an additional feature to all combined-movement equipment by eliminating the risks mentioned above. The invention relates to a device that modifies an alternating helical movement (or other movements) in the event of an overload on the instrument in the root canal, thus making sure that endodontic treatment is gradual, smooth and gentle.

In order to achieve this, the invention comprises an angle-piece head consisting of:

a head, a transmission shaft mounted so that it rotates in the head, an instrument holder sleeve that rotates and slides in the head with a movement along a transverse axis, a cam that engages the instrument holder sleeve and is driven by the transmission shaft and is off-centred with respect to the longitudinal axis of the transmission shaft;

a main transmission element that is rotated by the transmission shaft and is angularly flexible with respect to the longitudinal axis of the transmission shaft having, at its end, the cam, and being located between the instrument holder sleeve and the transmission shaft.

The device according to the invention gradually reduces the operating amplitude of the root canal instrument depending on the mechanical stress exerted on it. When the force exerted on the instrument becomes abnormally high, the operating amplitude of the instrument changes gradually until it is completely cancelled. The amplitude of the movement transmitted to the instrument is therefore damped and converted into a vibrational movement thus encouraging possible release of the instrument whilst eliminating any risk of breakage. This conversion of movement when excessively high forces are exerted on the instrument makes it possible to carry out, without risk, root canal finding, root canal drilling and other endodontic operating procedures.

This conversion of altrenating helical movement is obtained thanks to the flexibility of the main transmission element that is located between the instrument holder sleeve and the transmission shaft.

The present invention is distinguished by the fact that the safety of root canal treatment is based on deflection, the gradual bending of a main transmission element. This deformable element is:

the sensitive component that detects any abnormal resistance to the instrument;

the intelligent component of the equipment that converts movement, by automatically deforming, when the total force exerted on the instrument exceeds a specific amount.

This conversion of movement makes the safety of mechanised root canal treatment comparable to that of manual root canal treatment.

The description that follows and the accompanying drawings supplement and emphasise the originality of the invention that is described above together with its characteristics and advantages.

Figures 1, 2:
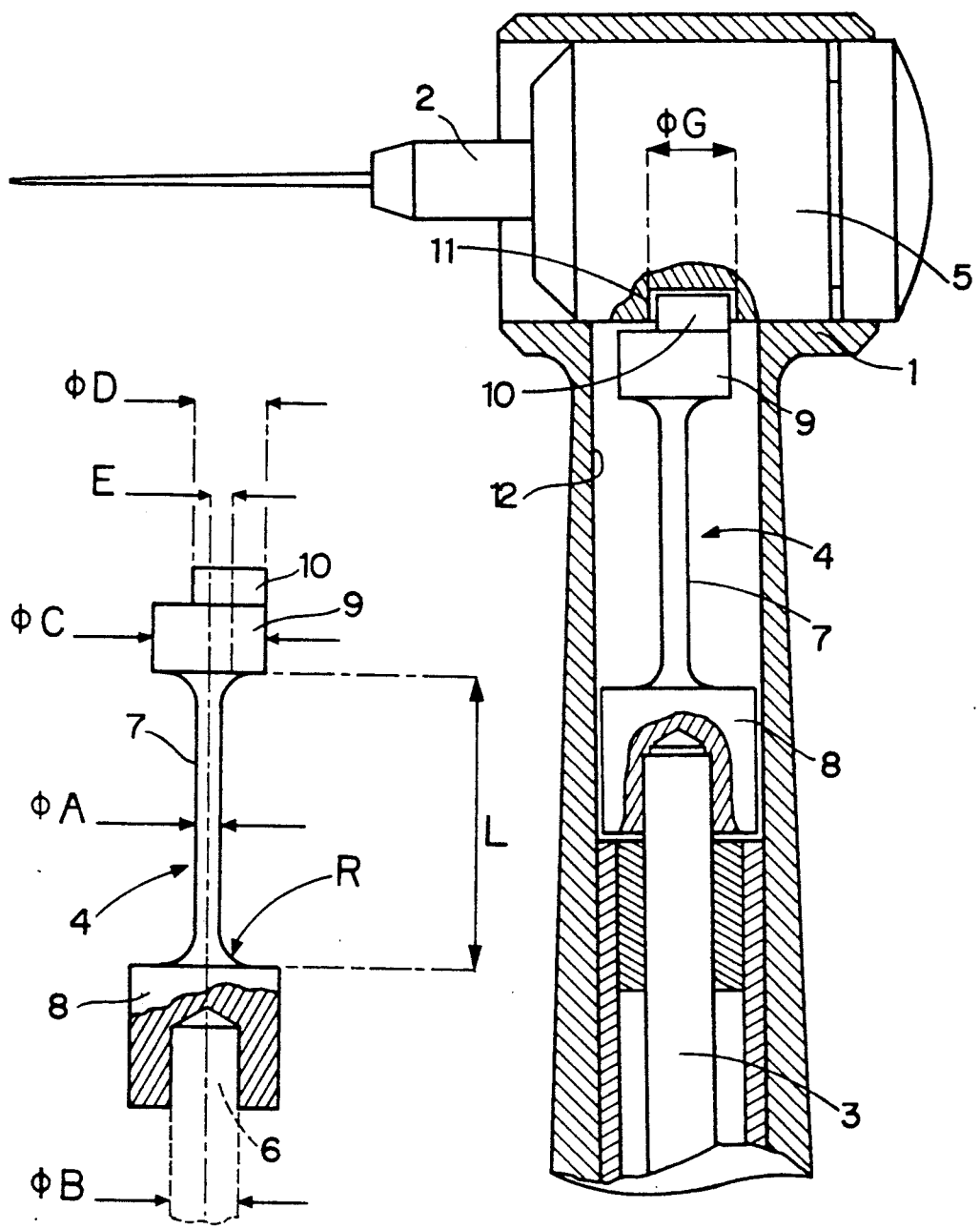
FIG. 1 is an axial section of the head including the mechanism that controls the convertible helical movement.
FIG. 2 is a view of the main transmission unit that becomes flexible when subjected to a force that exceeds the normal operating forces (this design is in no way exhaustive).
Figure 3:
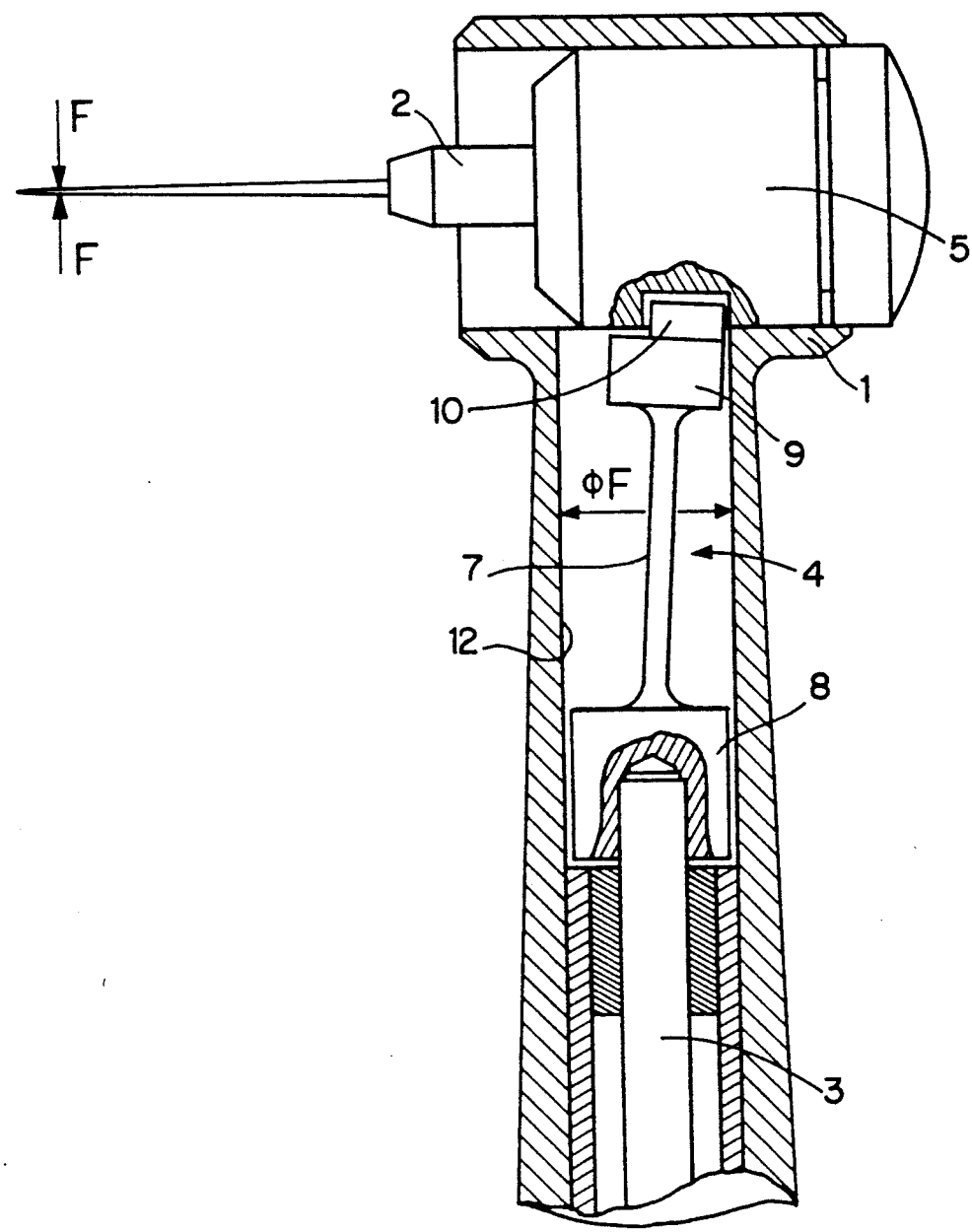
FIG. 3 is an axial section of the head showing the deformation of the flexible element in the event of an overload on the instrument together with the limitation of the angular deformation.

Such a mechanism can be accommodated in an angle-piece head 1 consisting of an instrument locking system 2 which can be a gate, thrust piece, pushbutton-operated clamp etc.

This angle-piece head fits on a case that may or may not be fitted with any speed reducing or speed increasing mechanism. This case allows connection of any type with an electric or pneumatic miniature motor, thus making it possible to drive a transmission shaft 3.

A flexible main transmission element 4 is fitted at the end of shaft 3 (the element 4 having, at one end, a hole 6 with diameter $\phi B$ the element 4 being clamped on transmission shaft 3 and pinned if applicable).

An instrument holder sleeve 5 can rotate and slide in head 1 along the transverse of head 1.

The main transmission element 4 consists of a rod whose reduced diameter is $\phi A$ between head 8 and a shoulder 9 whose diameter is $\phi C$. The end of transmission element consists of a cam 10 whose diameter is $\phi D$ that is off-centred by an amount E with respect to the longitudinal axis of transmission shaft 3 and engages instrument holder sleeve 5.

The instrument holder sleeve 5 can therefore produced an alternating helical movement along the transverse axis at right angles to the longitudinal axis of rotation of transmission shaft 3. Cylindrical instrument holder sleeve 5 has a cylindrical hole 11 having a diameter $\phi G$ that is perpendicular to and centrally aligned with the transverse axis of displacement. The end of cam 10 of the main transmission element 4 fits in the hole 11.

The combination of the instrument holder sleeve 5 and the main flexible transmission element 4 with a cam that is rotated by transmission shaft 3 constitutes the mechanism that transmits an alternating helical movement, that can be converted and damped, to instrument 2.

Main transmission element 4 with cam 10 has a flexible rod 7 which makes the transmission element 4 angularly flexible with respect to the longitudinal axis of transmission shaft 3. The flexible rod is made of a material with an appropriate modulus of elasticity. Its angular deformation is limited by a shoulder 9 on rod 7 of the main transmission element 4. This shoulder 9 can rest against the perimeter 12 of the head 1 whose diameter is $\phi F$. The materials used for the case of head 1, sleeve 5 and the main transmission element 4 with a cam offer extremely good frictional properties.

FIG. 2 shows one possible design of main transmission element 4 with a cam 10; rod 7 must be of sufficient length L to ensure optimum elasticity that is perfectly matched to the forces applied to instrument 2 so as to obtain optimum effectiveness root canal treatment operations.

Flexible main transmission element 4 with a cam 10 may be a single-piece unit or be made of various assembled parts.

The material used has a very good modulus of elasticity appropriate for the desired degree of safety so as to ensure optimum effectiveness of mechanised root canal treatment. The values of diameter $\phi A$, of radius R, and of length L vary depending on the heat treatment, type of metal, alloy or, if applicable, plastic.

The backlash between the diameter $\phi D$ of cam 10 and the diameter $\phi G$ of hole 11 of instrument holder sleeve 5 is necessary and functional.

The value of off-centre E of cam 10 with respect to the centreline of diameters $\phi B$, $\phi A$ and $\phi C$ of the main flexible transmission element 4 defines the amplitude of the alternating straight and circular movements. The modulus of elasticity of main transmission element 4 with a cam 10 defines the threshold for conversion of movement and the intensity of the vibrational movement.

The alternating helical movement of instrument holder sleeve 5 can be converted automatically, depending on force F applied to instrument 2, vibrational movement of which the frequency depends on the rotation speed of the drive system; the amplitude is therefore practically zero when the angular deformation of main transmission element 4 equals the value of off-centre E.

The amplitude of these longitudinal and angular movements can therefore be completely cancelled when main transmission element 4 with a cam 10 is deformed by an angular bending equivalent to off-centre E.

The equipment according to the invention makes mechanised root canal treatment safe by gradually reducing the working amplitude of root canal instrument 2 as a function of stress.

Endodontic treatment can therefore only be carried out progressively without instrument 2 being subjected to overloads caused either by the practitioner or by abnormally high resistance due to an obstacle in the root canal.

I claim:

1. An angle-piece for an endodontic instrument (2) comprising:
   a head (1),
   a transmission shaft (3) mounted so that it is guided and rotates in the head (1), the transmission shaft having a longitudinal axis,
   an instrument holder sleeve (5) that rotates about, and slides along, a transverse axis which is perpendicular to said longitudinal axis,
   a cam (10) that engages the instrument holder sleeve (5), said cam being driven by the transmission shaft (3), said cam being off-centred with respect to said longitudinal axis of the transmission shaft (3)
   wherein the angle-piece comprises a main transmission element the main transmission element being positioned between the cam and the transmission shaft (4), the main transmission element being made of a material having a modulus of elasticity, the main transmission element (4) being rotated by the transmission shaft (3) and being angularly and freely flexible in the head (1) with respect to said longitudinal axis of the transmission shaft (3), at its end,
   wherein, when forces (F) are applied to the instrument (2), bending of main transmission element (4) reduces an amplitude of movement of the instrument holder sleeve (5) and of the instrument (2).

2. The angle-piece of claim 1, wherein the modulus of elasticity of the material of which the main transmission element (4) is made is such that the main transmission element (4) bends when subjected to a force that exceeds the normal working force.

3. The angle-piece of claim 1, wherein the main transmission element (4) includes a flexible rod (7) with a shoulder (9).

4. The angle-piece of claim 3, wherein the shoulder (9) of the main transmission element (4) may rest against an interior perimeter (12) of the head (1) in order to limit angular bending of the main transmission element (4).

5. The angle-piece of claim 1, wherein the instrument holder sleeve (5) has a hole (11) in which the end of the cam (10) of the main transmission element (4) fits.

6. The angle-piece of claim 5, wherein the hole (11) is cylindrical.

7. The angle-piece of claim 6, wherein functional backlash is provided between the cam (10) and the hole (11) in the instrument holder sleeve (5).

8. The angle-piece of claim 1, wherein the main transmission element (4) is a single-piece unit and is joined to the transmission shaft (3).

9. The angle-piece of claim 1, wherein the main transmission element (4) is clamped to an end of the transmission shaft (3).

10. An angle-piece for an endodontic instrument (2) comprising:
    a head (1),
    a transmission shaft (3) mounted for rotation in the head (1), the transmission shaft having a longitudinal axis,
    an instrument holder sleeve (5) that rotates about, and slides along, a transverse axis which is perpendicular to said longitudinal axis, and
    a transmission element (4), the transmission element having first and second ends, the first end being connected to the transmission shaft (3), the second end having a cam (10) which engages a hole (11) in the instrument holder sleeve, the cam (10) being off-centred with respect to said longitudinal axis, wherein the transmission element includes a flexible rod (7) which directly connects the first and second ends of the transmission element, wherein displacement of the cam (10) relative to said longitudinal axis causes displacement of the flexible rod (7) relative to said longitudinal axis.

11. In an angle-piece for an endodontic instrument (2), the angle-piece including a head (1), a transmission shaft (3) mounted for rotation in the head (1), the transmission shaft having a longitudinal axis, an instrument holder sleeve (5), and a transmission element (4), the transmission element having a first end connected to the transmission shaft (3) and a second end having a cam (10) which engages a hole (11) in the instrument holder sleeve (5), the cam (10) being off-centred with respect to said longitudinal axis, the improvement wherein the transmission element includes a flexible rod (7) which connects the first and second ends of the transmission element, wherein the cam is free to move with displacement of the flexible rod, and wherein displacement of the cam (10) relative to the longitudinal axis causes a corresponding displacement of the flexible rod (7) relative to the longitudinal axis.

* * * * *